United States Patent
Haney et al.

(10) Patent No.: US 7,056,440 B2
(45) Date of Patent: Jun. 6, 2006

(54) DIALYSIS DEVICE WITH AIR CHAMBER

(75) Inventors: Paul J. Haney, Beloit, WI (US); William Klungle, Grand Haven, MI (US)

(73) Assignee: Pierce Biotechnology, Inc., Rockford, IL (US)

( * ) Notice: Subject to any disclaimer, the term of this patent is extended or adjusted under 35 U.S.C. 154(b) by 0 days.

(21) Appl. No.: 11/075,084

(22) Filed: Mar. 8, 2005

(65) Prior Publication Data

US 2005/0199550 A1 Sep. 15, 2005

Related U.S. Application Data

(60) Provisional application No. 60/551,603, filed on Mar. 9, 2004.

(51) Int. Cl.
*B01D 61/24* (2006.01)
*B01D 61/28* (2006.01)

(52) U.S. Cl. .............. 210/644; 210/232; 210/242.1; 210/321.6

(58) Field of Classification Search ........... 210/232, 210/321.6, 321.61, 321.72, 321.75, 321.84, 210/455, 477, 242.1, 500.21; 422/101, 102, 422/104
See application file for complete search history.

(56) References Cited

U.S. PATENT DOCUMENTS

| | | | |
|---|---|---|---|
| 3,804,258 A * | 4/1974 | Okuniewski et al. | 210/460 |
| 4,419,237 A | 12/1983 | Esmond | 210/321.2 |
| 4,597,868 A * | 7/1986 | Watanabe | 210/232 |
| 4,721,555 A * | 1/1988 | Grosshandler | 204/252 |
| 4,828,706 A | 5/1989 | Eddleman | |
| 5,085,753 A * | 2/1992 | Sherman | 204/267 |
| 5,324,428 A | 6/1994 | Flaherty | |
| 5,503,741 A | 4/1996 | Clark | |
| 5,783,075 A | 7/1998 | Eddleman et al. | |
| 6,039,871 A | 3/2000 | Sykaluk | 210/321.71 |
| 6,086,770 A * | 7/2000 | Matkovich | 210/645 |

(Continued)

FOREIGN PATENT DOCUMENTS

DE 2039050 2/1972

(Continued)

OTHER PUBLICATIONS

EPO, *International Search Report and Written Opinion of the International Searching Authority*, International Application No. PCT/US2005/007609, Mailed on Aug. 1, 2005 (17 pages).
EPO, *Partial International Search Report*, International Application No. PCT/US2005/007609, mailed on Mar. 8, 2005 (5 pages).

*Primary Examiner*—John Kim
(74) *Attorney, Agent, or Firm*—Wood, Herron & Evans, LLP

(57) ABSTRACT

A device for the dialysis of a sample includes a hermetically sealed sample chamber formed by a gasket with dialysis membranes affixed to each side in facing relationship. The gasket is impermeable to the sample being dialyzed, but is penetrable and reusable such that a sample introduction mechanism can be inserted through the gasket into the chamber, and then withdrawn without sample being permitted to leak. The device is fitted into a rigid housing containing windows and at least one port parallel to the dialysis membranes for directing the sample introduction mechanism into the gasket. The housing includes at least one pressure ridge for assisting in hermetically sealing the sample chamber and air chamber at one end for causing the device to float in an upright position when immersed in a dialysate.

14 Claims, 3 Drawing Sheets

U.S. PATENT DOCUMENTS

| | | |
|---|---|---|
| 6,368,509 B1 | 4/2002 | Bansal et al. |
| 6,531,061 B1 | 3/2003 | Cholewa ..................... 210/232 |
| 2003/0133846 A1 | 7/2003 | Ben-Asouli et al. |
| 2005/0092666 A1* | 5/2005 | Wilson ....................... 210/136 |

FOREIGN PATENT DOCUMENTS

| | | |
|---|---|---|
| EP | 0402611 | 12/1990 |
| WO | WO9508385 | 3/1995 |

\* cited by examiner

DIALYSIS DEVICE WITH AIR CHAMBER

RELATED APPLICATIONS

This application claims the benefit of U.S. Provisional Application No. 60/551,603 filed Mar. 9, 2004 which is herein incorporated by reference in its entirety.

FIELD

The present invention relates to a device for the dialysis of small, fixed-volume samples such as those commonly dialyzed in the research laboratory. The device, which can be disposable, offers convenience in loading and unloading of sample and offers accelerated dialysis of sample. The device can be submerged and moved freely in dialysate held in a vessel of the user's choice such as a beaker.

BACKGROUND

It has been known for some time that molecules of various molecular weights can be separated across a semi-permeable membrane. The membrane by virtue of its composition, and consequently its porosity, allows molecules equal to or less than a particular molecular weight to pass through the membrane. Larger molecules are unable to pass through. This has led to four common applications of dialysis membranes: 1) exchanging one sample buffer for another buffer, 2) sample desalting, 3) molecular separations, and 4) sample concentration. These applications are most often utilized in the area of laboratory research and the dialysis of patient bodily fluids such as blood.

Various methods have been developed so that a dialysis membrane is the sole pathway of molecular exchange between a sample and dialysate. The most widely used method in the research laboratory is taking the dialysis membrane which is molded in the shape of a tube and tying, or clamping, one end of the tube to form a sack. The sample solution is added to the interior of the dialysis membrane sack which is then tied or clamped at the other end which had remained open. The sack, now a closed vessel, is submerged into the dialysate.

The method described above has significant drawbacks. The tying or clamping of the ends of the dialysis membrane tubing requires skill. If the end of the tubing is not carefully tied, the sack will leak and the sample can be lost. Also, it is difficult to load and unload the sample from the sack because the membrane is flaccid; samples are often spilled during these steps. Touching the dialysis tubing membrane with fingers can also affect the sample dialysis. Therefore it requires skill to touch as little of the membrane as possible when tying or clamping it. An alternative is to wear gloves; however, it also requires skill to tie the tubing while wearing gloves. Since the sample chamber of the dialysis tubing membrane is open during the loading and unloading of sample, the sample can be contaminated with any substance in the environmental air. It would be desirable to have a sample chamber which is hermetically sealed and to add the sample with a device such as a syringed needle. Also, wetted dialysis membrane tubing can not be labeled so labeling must be written on a small clamp or on an object which is inconveniently attached to the tubing with material such as string.

In order to address some of the problems with loading sample into and unloading sample from dialysis tubing as described above, one company has offered commercially preformed dialysis sacks. These sacks are dialysis tubing which has already been clamped at one end and at the open end a funnel has been attached. After the sample is loaded through the funnel, the tubing is clamped below the funnel and dialysis proceeds. Although the loading and unloading of sample are somewhat simplified, the product still suffers the other problems as described above for dialysis tubing.

Another commercially available product has taken another approach to addressing some of the inconvenience of the dialysis tubing and the pre-formed dialysis tubing sack. Two concentric rings, one larger than the other, trap a sheet of membrane between the rings when the outer ring is tightened upon the inner ring. A vessel is formed such that the rings form the walls of the vessel and the floor is the dialysis membrane. The vessel then is floated on top of the dialysate and sample is added to the interior of the floating vessel. Although this solution offers advantages, it introduces new problems. First, the sample may be open to the environmental air which would allow it to be easily contaminated. Secondly, because the vessel is open, it is easy for the sample to spill into the dialysate as it floats. Loading and unloading are greatly simplified, but assembly of the device requires some skill by the user.

Of the devices described above, none permit the convenient loading and unloading of small, fixed-volume samples to be dialyzed in the research laboratory. Also, none protect the sample from contamination during loading and unloading. To address these disadvantages, U.S. Pat. No. 5,503,741 owned by Pierce Biotechnology Incorporated discloses a dialysis device having a hermetically sealed vacant chamber. The chamber is formed by a gasket with dialysis membranes affixed to each side in facing relationship. The gasket is impermeable to the sample being dialyzed, but is penetrable and reusable such that a sample introduction mechanism can be inserted through the gasket into the chamber and then withdrawn without the sample being permitted to leak. In this fashion, convenient loading and unloading of small, fixed-volume samples into the chamber is accomplished while avoiding contamination. This application provides further enhancements to the dialysis device having a hermetically sealed chamber.

SUMMARY

This application relates to a device for the dialysis of a sample. The device embodies a hermetically sealed sample chamber formed by a gasket with dialysis membranes affixed to each side in a facing relationship. In one preferred embodiment, the membranes are in a substantially parallel relationship. The gasket is impermeable to the sample being dialyzed, but penetrable and of sufficient thickness such that a sample introducing mechanism can be inserted through the gasket into the chamber. The device further comprises at least one pressure ridge integrally formed on at least one of a pair of plates which form a housing for the chamber. The at least one pressure ridge is configured to enhance the hermetic seal of the chamber.

In a further embodiment, the device includes an air chamber formed by the pair of plates that provide the housing. The air chamber causes the device to float in an upright position when the device is immersed in a dialysate.

DESCRIPTION OF THE PREFERRED EMBODIMENT

Figure 1:
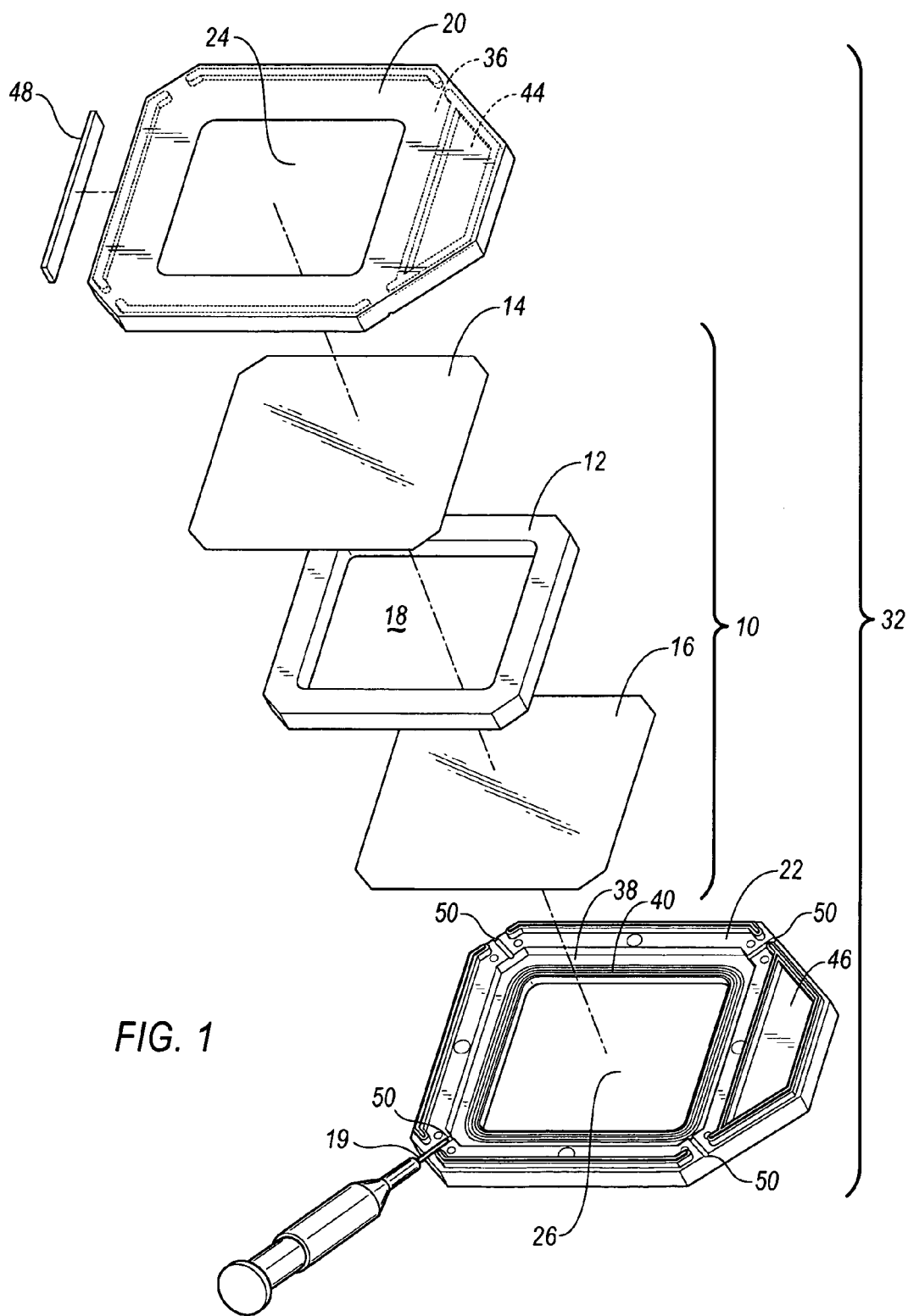
FIG. 1 is an exploded perspective view of a dialysis device with an air chamber according to an embodiment.
Figure 2:
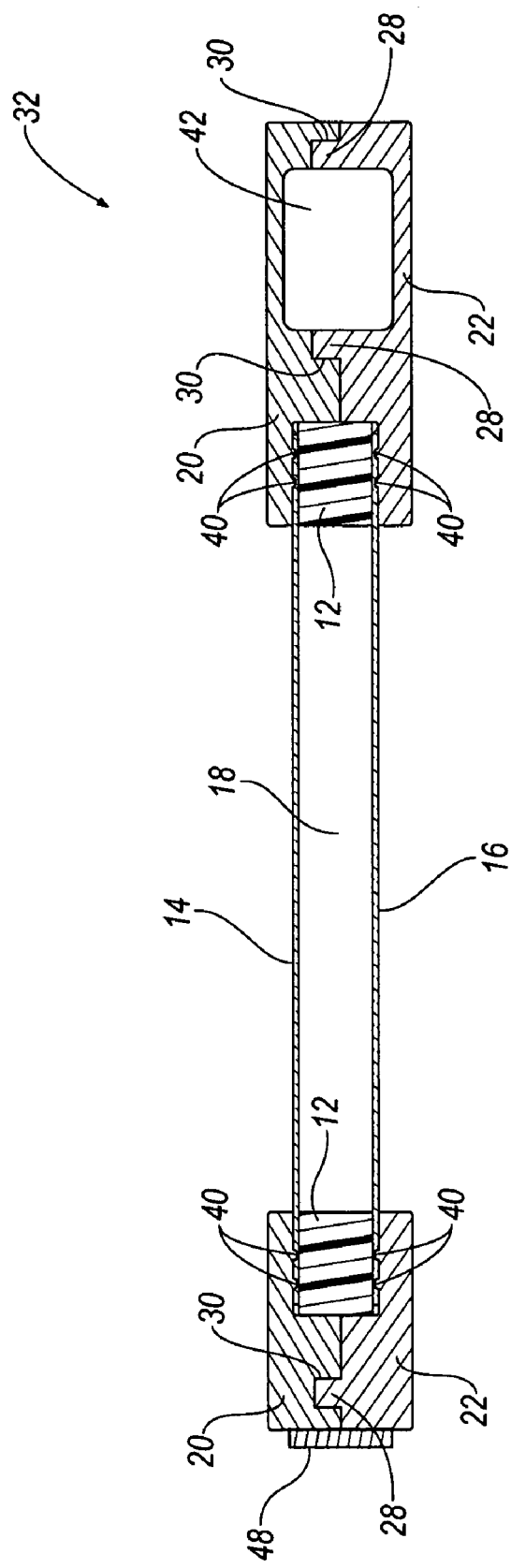
FIG. 2 is a cross-sectional side view of the device of FIG. 1.

Turning to the drawings, FIG. 1 illustrates an exploded view of a dialysis device, shown generally at 10, according to an embodiment of the invention. The device includes a gasket 12 and a pair of dialysis membranes 14, 16. As illustrated in FIG. 2, in assembled form the dialysis membranes 14, 16 are affixed to each side of the gasket 12 to form a chamber 18 therebetween. Thus, membranes 14, 16 are in a facing relationship with respect to one another. In one preferred embodiment, the membranes are in a substantially parallel relationship.

One aspect of the invention is that the chamber 18 formed by the membranes 14, 16 and the gasket 12 is hermetically sealed and that the gasket 12 is capable of being penetrable by a sample introduction mechanism such as a syringed needle 19 in the illustrated embodiment. In the illustrated embodiment, syringed needle 19 can then be inserted through the gasket 12 into the chamber for delivery of sample and then withdrawn without sample being permitted to leak. To this end, the gasket 12 should be a material that is pliable with high memory function, for example, rubber, plastic or Silicone. Turning to the membranes 14, 16, customary dialysis membranes, commonly derived from regenerated cellulose, are useful. In order to achieve a hermetically sealed chamber, the membranes 14, 16 are securely affixed to the gasket 12 such as through the mechanism of adhesive bonding or a molding operation. Particular embodiments of the device may not require adhesive bonding or a molding operation due to the manner in which the device is constructed.

While the device described above, comprising the hermetically sealed chamber 18 formed by the gasket 12 and membranes 14, 16, can be directly used for dialyzing a sample, preferably the device is fitted into a rigid housing formed by a pair of plates 20, 22. The housing structurally stabilizes the device 10 for facilitating handling, permits affixing identifying indicia and, perhaps most importantly, allows for directed needle insertion to minimize the probability of needle penetrations through the membranes 14, 16. Each of the plates 20, 22 contain windows 24, 26, respectively, positioned opposite the membranes 14, 16 of the device 10.

As best shown in FIG. 2, in the illustrated embodiment alignment of the plates 20, 22 can be achieved through a tongue 28 and groove 30 arrangement. The plates 20, 22 can be sealed so as to firmly sandwich the device 10 within housing to form a completed assembly 32 by means of sonic welding, adhesive or the like.

Another aspect of the invention is that each of the plates 20, 22 also includes a ledge 36, 38, respectively, in which the gasket 12 resides in the completed assembly 32. To provide an enhanced hermetically sealed chamber, each ledge 36, 38 includes one or more raised areas or pressure ridges 40 preferably located along a central portion of each ledge 36, 38 for engaging the gasket 12 in the completed assembly 32. In the illustrated embodiment, a pair of pressure ridges 40 extend along the periphery of each window 24, 26. However, it will be appreciated that the invention can be practiced with any desired number of pressure ridges 40 extending along the entire periphery, or a portion of the periphery of each window 24, 26. For example, a larger number of pressure ridges 40 provide greater protection against the transfer of fluid between each plate 20, 22 and the gasket 12. In addition, the invention can be practiced with one or more pressure ridges 40 located on only one ledge, rather than both ledges. Other variations of the pressure ridges 40 are contemplated by the inventors and are within the scope of the invention.

Another aspect of the invention is that the completed assembly 32 includes an air chamber 42 formed by each plate 20, 22 of the completed assembly 32. Specifically, each plate 20, 22 includes corresponding air pockets 44, 46, respectively, that together form the air chamber 42 when each plate 20, 22 is brought together to form the completed assembly 32. Alignment of the plates 20, 22 is achieved through the tongue 28 and groove 30 arrangement. The air chamber 42 can be sealed by the plates 20, 22 by means of sonic welding, adhesive or the like. Thus, the air chamber 42 is integrally formed with the plates 20, 22. In operation, the air chamber 42 causes the device 10 to float in an upright or vertical position when the completed assembly 32 is placed in a dialysate (not shown). In a preferred embodiment, the plates 20, 22 are formed form Acrylonitride Butadiene Styrene (ABS) wherein the buoyancy characteristic of the plates 20, 22 would allow for the sample chamber 18 to be fully immersed in the dialysate while the air chamber 42 keeps the device 10 afloat. Other materials may be used to form the plates 20, 22, for example, plastic or other polymeric material. A weight 48 can be placed on an opposite end of the completed assembly 32 to that of the air chamber 42 to further assist in causing the device 10 to float in the upright position. The weight 48 should be sufficiently heavy to cause the completed assembly 32 to be suspended in the upright or vertical position in the dialysate. However, the weight 48 should not be so heavy such that the completed assembly 32 is completely submerged in the dialysate. Preferably, the weight 48 is sufficiently heavy to cause the top of the completed assembly 32 to extend above the top of the dialysate so that the completed assembly 32 can be easily removed from the dialysate.

As illustrated, the housing, when assembled, contains one or more needle ports 50 for directing and guiding a needle into the gasket 12 and, in turn the chamber 18. Each needle port 50 runs between the membranes 14, 16 and is substantially perpendicular to the edge of the gasket 12 so that the needle can access the chamber 18 without contacting either of the membranes 14, 16. Also, each needle port 50 is positioned higher in elevation than the pressure ridges 40 so that the needle can also access the chamber 18 without inadvertently contacting the pressure ridges 40. Preferably, as shown in FIG. 1, each needle port 50 meets the edge of the gasket 12 at a corner so that, by tilting the assembly 32, sample can be collected in the corner and withdrawn. Preferably, the housing is formed of a lightweight and durable material such plastic or other polymer which can be molded into the plates 20, 22 having the pressure ridges 40.

An example of the use of the device 10 described above would be the exchange of a buffer, in which a protein sample resided, for another buffer. The protein in buffer "A" would be injected into the hermetically sealed sample chamber of the device and, then, the device 10 would be submerged (weight 48 end first) into buffer "B" (dialysate) that is contained in a vessel, such as a beaker, such that the air chamber 42 causes the assembly 32 to float in the dialysate. The protein being larger than the dialysis membrane pores would be retained within the sample chamber 18, while the buffer molecules within the sample chamber 18 would exchange by diffusion with the buffer molecules in the dialysate.

The completed assembly 32 described herein is easily handled by the user and requires no special skill. Samples are loaded and unloaded with a needle and syringe and during the process fingers never come in contact with the membranes 14, 16, but only the housing surrounding the membranes 14, 16. Since the completed assembly 32 is rigid and hermetically sealed, the spilling of sample is improbable. Also, because the sample chamber is hermetically sealed with the assistance of the pressure ridges 40, and the sample loaded and unloaded with a needle and syringe, the sample cannot be contaminated with any substance in the environmental air. The housing surrounding the sample chamber 18 is of ample size that allows for the easy labeling of the sample with commonly used scientific marking pens. The rigidity of the housing of the invention positions the membranes 14, 16 so that they are parallel to each other and separated only by the thickness of the gasket 12. The result is that the sample chamber 18 of the device 10 has a high surface to volume ratio. Compared to dialysis tubing which assumes a cylindrical shape when loaded with sample, the higher surface to volume of the device 10 of the invention results in faster dialysis times.

Figure 3:
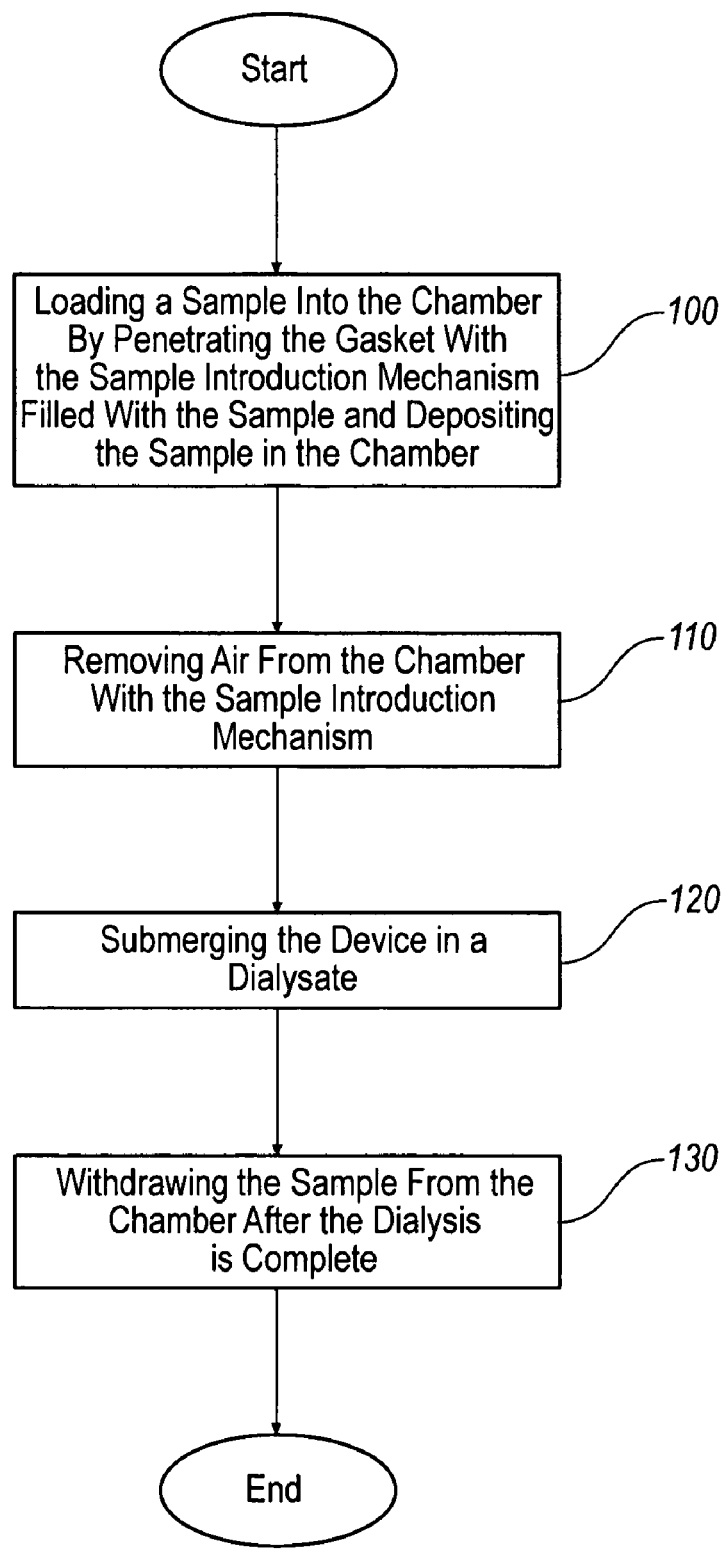
FIG. 3 illustrates a method of using the dialysis device of FIG. 1.

FIG. 3 illustrates a method of using the device 10 for accomplishing dialysis of a sample. At step 100, the sample is loaded into the device 10 by sliding a needle through one of the needle ports 50, in the housing, through the side of the wall of the gasket 12, which also serves the function of a self-sealing septum. Once the needle passes through the gasket wall and penetrates the sample chamber 18, the plunger of the syringe is depressed and the sample transferred from the barrel of the syringe into the sample chamber 18. The method advances to step 110.

To effectively execute the dialysis, it is preferable to remove any air that was in the sample chamber 18 before the sample was loaded. At step 110, the plunger of the syringe is pulled back to draw the air through the needle that is positioned so that it is in direct contact with the air bubble in the sample chamber 18. Once the air is removed and the sample is in contact with the maximum amount of the membranes 14, 16, the method advances to step 120.

At step 120, the device 10 is submerged into the dialysate. Preferably, the end of the assembly 32 having the weight 48 is first immersed in the dialysate such that the assembly 32 is in an upright position and the top of the completed assembly 32 extends above the dialysate. In this manner, the device 10 can be easily removed from the dialysate by grasping the top of the completed assembly 32. The dialysate is held in a vessel, such as a beaker, and mixing of the dialysate can be incorporated to insure a fresh molecular layer of dialysate in contact with the membranes 14, 16. Because of the devices self-contained nature it can easily be transferred to a vessel containing fresh dialysate which has the effect of accelerating the dialysis. Alternatively, the device 10 can be pulled from the dialysate while it is poured from the vessel and fresh dialysate added. After the dialysis of the sample is complete, the device 10 is removed from the vessel containing the dialysate. Next, the method advances to step 130.

At step 130, and the needle slid through one of the needle ports 50, in the housing, through the side of the gasket wall. When the needle has passed through the gasket 12 and makes contact with the sample, the plunger is drawn back so that the sample is drawn into the syringe barrel. The needle is positioned in the sample chamber 18 so that all sample feeds into the needle and sample recovery is essentially complete.

While the invention has been specifically described in connection with certain specific embodiments thereof, it is to be understood that this is by way of illustration and not of limitation, and the scope of the appended claims should be construed as broadly as the prior art will permit.

What is claimed is:

1. A device for the dialysis of a sample comprising:
a hermetically sealed sample chamber formed by a gasket with dialysis membranes disposed on each side of said gasket, said gasket being impermeable to the sample being dialyzed, but penetrable and of sufficient thickness such that a sample introducing mechanism can be inserted through the gasket into the chamber, wherein said device further comprises at least one pressure ridge integrally formed on at least one of a pair of plates that provide a housing for said sample chamber, said at least one pressure ridge configured to enhance the hermetic seal of said sample chamber, each of said pair of plates having a window positioned opposite a respective one of said membranes, and an air chamber formed by said pair of plates, said air chamber causing the device to float in a generally upright position when the device is immersed in a dialysate.

2. The device of claim 1 wherein said dialysis membranes are in substantially parallel relationship with said gasket.

3. The device of claim 1 wherein said sample introduction mechanism is a syringed needle.

4. The device of claim 1 wherein each of said plates includes a ledge upon which said gasket is seated, said at least one pressure ridge being formed on at least one of said ledges.

5. The device of claim 1 wherein said housing provides at least one port that communicates with said gasket, said at least one port being positioned higher in elevation than the said at least one pressure ridge.

6. The device of claim 5 wherein said at least one port is configured to receive said sample introduction mechanism therethrough.

7. The device of claim 5 wherein said at least one port is configured to receive a syringed needle therethrough.

8. The device of claim 1 where said pair of plates are formed of a lightweight and durable moldable material.

9. The device of claim 8 wherein said material is Acrylonitride Butadiene Styrene.

10. The device of claim 1 wherein said gasket is formed of a pliable material with high memory function.

11. The device of claim 10 wherein said material is rubber or silicone.

12. A device for the dialysis of a sample comprising:
a hermetically sealed sample chamber formed by a gasket with dialysis membranes disposed on each side of said gasket in substantially parallel relationship without any additional supporting structure there between, said gasket being impermeable to the sample being dialyzed, but penetrable and of sufficient thickness such that a needle can be inserted through the gasket into the chamber, wherein said device further comprises an air chamber formed by a pair of plates that provide a housing for said sample chamber, said air chamber causing the device to float in an upright position when the device is immersed in a dialysate, each of said pair of plates having a window positioned opposite a respective one of said membranes.

13. A method of using a device for dialysis comprising a hermetically sealed sample chamber formed by a gasket with dialysis membranes disposed on each side of the gasket in a facing relationship without any additional supporting structure there between, the gasket being impermeable to the sample being dialyzed, but penetrable and of sufficient thickness such that a sample introduction mechanism can be inserted through the gasket into the chamber, and an air chamber formed by a pair of plates that provide a housing for the sample chamber, each of said pair of plates having a window positioned opposite a respective one of said membranes, said method comprising the steps of:

loading a sample into the sample chamber by penetrating the gasket with the sample introduction mechanism filled with the sample and depositing the sample in the sample chamber;

removing air from the sample chamber with the sample introduction mechanism;

removing the sample introduction mechanism from the sample chamber;

immersing the device in a dialysate;

floating the device in a generally upright position in the dialysate by said air chamber; and withdrawing the sample from the sample chamber after the dialysis is complete.

14. The method of claim 13 further comprising the step of: mounting a weight on the device.

* * * * *